US007790193B2

(12) United States Patent
Melvik et al.

(10) Patent No.: US 7,790,193 B2
(45) Date of Patent: Sep. 7, 2010

(54) USE OF ALGINATE MATRICES TO CONTROL CELL GROWTH

(75) Inventors: Jan Egil Melvik, Oslo (NO); Michael Dornish, Bekkestua (NO)

(73) Assignee: FMC Biopolymer AS, Drammen (NO)

( * ) Notice: Subject to any disclaimer, the term of this patent is extended or adjusted under 35 U.S.C. 154(b) by 1629 days.

(21) Appl. No.: 11/020,622

(22) Filed: Dec. 23, 2004

(65) Prior Publication Data

US 2005/0169895 A1    Aug. 4, 2005

Related U.S. Application Data

(60) Provisional application No. 60/531,917, filed on Dec. 23, 2003.

(51) Int. Cl.
*A61F 2/02* (2006.01)
(52) U.S. Cl. ................................................... 424/423
(58) Field of Classification Search ........................ None
See application file for complete search history.

(56) References Cited

U.S. PATENT DOCUMENTS

| | | | |
|---|---|---|---|
| 5,459,054 A | 10/1995 | Skjak-Braek et al. |
| 5,531,716 A | 7/1996 | Luzio et al. |
| 5,643,594 A | 7/1997 | Dorian et al. |
| 5,900,238 A | 5/1999 | Gombotz et al. |
| 6,638,917 B1 | 10/2003 | Li et al. |
| 2003/0143274 A1 | 7/2003 | Viegas et al. |

FOREIGN PATENT DOCUMENTS

WO    98/23226 A1    6/1998

WO    99/15211 A1    4/1999

OTHER PUBLICATIONS

Sakurai et al, "production of 4,5-dihyrdoxyphthalate by Pseudomonas testosteroni Immobilized in Alginate Gel bead", Biochemical Engineering Journal, vol. 3, Issue, Jun. 1999, pp. 235-238.*
The 6th International Congress of "The Cell Transplant Society", Final Program/Abstract Volume, Mar. 2-5, 2003 Grand Hyatt Atlanta, Atlanta Georgia, Cover Page and pp. 56 and 57.

(Continued)

*Primary Examiner*—Carlos A Azpuru
(74) *Attorney, Agent, or Firm*—FMC Corporation

(57) ABSTRACT

Methods of inhibiting proliferation of a plurality of proliferating cells are disclosed. Methods of inhibiting cell overgrowth on compositions that are in an animal's body are disclosed. Methods of inhibiting cell overgrowth on a device that is in an animal's body are disclosed. Devices that have on their exterior surface an alginate matrix that comprises Strontium are disclosed. Compositions comprising an alginate body and alginate sheets that each comprise a single layer of cells coating the exterior surface of the alginate body are disclosed. Methods of preparing an artificial tissue are disclosed. Devices comprising cells encapsulated within an alginate matrix and/or maintained as a monolayer on an alginate body, and methods of making and using the same are disclosed. Methods of coating compositions and devices are disclosed.

4 Claims, 7 Drawing Sheets

OTHER PUBLICATIONS

Adhesion and Growth of Bone Marrow Stromal Cells on Modified Alginate Hydrogels; M.A. Lawson, Ph.D., Tissue Engineering, vol. 10, No. 9/10, 2004, Mary Ann Liebert, Inc., pp. 1480 to 1491.
Alsberg et al., "Engineering growing tissues" *Proc Natl Acad Sci USA* (2002) 99:12025-12030.
Attramadal "The effect of divalent cations on cell adhesion" J Periodontal Res (1969) 4:281-285.
Cai et al., "Treatment of liver failure in rats with end-stage cirrhosis by transplantation of immortalized hepatocytes" *Hepatology* (2002) 36:386-394.
Canaple et al., "Development of a coculture model of encapsulated cells" *Ann NY Acad Sci* (2001) 944:350-361.
Constantinidis et al., "Effects of alginate composition on the metabolic, secretory, and growth characteristics of entrapped .beta.TC3 mouse insulinoma cells" *Biomaterials* (1999) 20:2019-2027.
Diamond et al., "Endoscopic correction of vesicoureteral reflux in children using autologous chondrocytes: preliminary results" *J. Urol* (1999) 162:1185-1188.
Dornish et al., "Standards and guidelines for biopolymers in tissue-engineered medical products: ASTM alginate and chitosan standard guides. American Society for Testing and Materials" *Ann NY Acad Sci* (2001) 944:388-397.
Emerich et al., "Update on immunoisolation cell therapy for CNS diseases" *Cell Transplantation* (2001) 10:3-24.
Emerich "Cell transplantation for Parkinson's disease" *Cell Transplant* (2002) 11:1-3.
Emerich et al. "A novel approach to neural transplantation in Parkinson's disease: use of polymer-encapsulated cell therapy" *Neurosci Biobehav Rev* (1992) 16:437-447.
Fragonas et al., "Articular cartilage repair in rabbits by using suspensions of allogenic chondrocytes in alginate" *Biomaterials* (2000) 21:795-801.
Hagihara et al., "Transplantation of xenogeneic cells secreting beta-endorphin for pain treatment: analysis of the ability of components of complement to penetrate through polymer capsules" *Cell Transplant* (1997) 6:527-530.
Hashimoto et al., "Peripheral nerve regeneration through alginate gel: analysis of early outgrowth and late increase in diameter of regenerating axons" *Brain Res.* (2002) 145:356-368.
Hynes "Integrins: bidirectional, allosteric signaling machines" *Cell* (2002) 110:673-687.
Kataoka et al., "Alginate, a bioresorbable material derived from brown seaweed, enhances elongation of amputated axons of spinal cord in infant rats" *J. Biomed Mater Res.* (2001) 54:373-384.
Lanza et al., "Xenotransplantation of cells and tissues: application to a range of diseases, from diabetes to Alzheimer's" *Molecular Medicine Today* (1999) 4:39-45.
Loebsack et al., "In vivo characterization of a porous hydrogel material for use as a tissue bulking agent" *Journal of Biomedical Materials Research* (2001) 57:575-581.
Miralles et al., "Sodium alginate sponges with or without sodium hyaluronate: in vitro engineering of cartilage" *J. of Biomedical Materials Research* (2001) 57:268-278.
O'Connor et al., "Survival and neurite outgrowth of rat cortical neurons in three-dimensional agarose and collagen gel matrices" *Neurosci Lett* (2001) 304:189-193.
Orive et al., "Cell encapsulation: promise and progress" *Nature Medicine* (2003) 9:104-107.
Read et al., "Local endostatin treatment of gliomas administered by microencapsulated producer cells" *Nat Biotechnol* (2001) 19:29-34.
Read et al., "Cells encapsulated in alginate: a potential system for delivery of recombinant proteins to malignant brain tumours" *Int J Devl Neuroscience* (1999) 17:653-663.
Risbud et al., "Islet immunoisolation: experience with biopolymers" *J. Biomater Sci Polymer Edn* (2001) 12:1243-1252.
Rokstad et al., "Microencapsulation of cells producing therapeutic proteins: optimizing cell growth and secretion" *Cell Transplant* (2002) 11(4):313-324.
Rokstad et al., "Transplantation of alginate microcapsules with proliferating cells in mice: capsular overgrowth and survival of encapsulated cells of mice and human origin" *Ann NY Acad Sci* (2001) 944:216-225.
Rowley et al., "Alginate type and RGD density control myoblast phenotype" *J. of Biomedical Materials Research* (2003) 60:217-223.
Rowley et al., "Alginate hydrogels as synthetic extracellular matrix materials" *Biomaterials* (1999) 20:45-53.
Sambanis "Engineering challenges in the development of an encapsulated cell system for treatment of type 1 diabetes" *Diabetes Technol Ther* (2000) 2(1):81-89.
Shapiro et al., "Novel alginate sponges for cell culture and transplantation" *Biomaterials* (1997) 18:583-590.
Siebers et al., "Analysis of the cellular reaction towards microencapsulated xenogeneic islets after intraperitoneal transplantation" *Journal of Molecular Medicine* (1999) 77:215-218.
Skaugrud et al., "Biomedical and pharmaceutical applications of alginate and chitosan" *Biotechnol Genet Eng Rev* (1999) 16:23-40.
Skjåk-Braek et al., "Application of alginate gels in biotechnology and biomedicine" *Carbohydrates in Europe* (1996) 14:19-25.
Smidsrød et al., "Alginate as Immobilization Matrix for Cells" *Tibtech* (1990) 8:71-78.
Stabler et al., "The effects of alginate composition on encapsulated betaTC3 cells" *Biomaterials* (2001) 22:1301-1310.
Stabler et al., "Effects of alginate composition on the growth and overall metabolic activity of betaTC3 cells" *Ann NY Acad Sci* (2002) 961:130-133.
Strand et al., "Alginate as immobilizing matrix for cells" *Minerva Biotechnologica* (2000) 12:223-233.
Strand et al., "Visualization of alginate-poly-L-lysine-alginate microcapsules by confocal laser scanning microscopy" *Biotechnol Bioeng* (2003) 82:386-394.
Sufan et al., "Sciatic nerve regeneration through alginate with tubulation or nontubulation repair in cat" *Journal of Neurotrauma* (2001) 18:329-338.
Uludag et al., "Technology of mammalian cell encapsulation" *Adv Drug Deliv Rev* (2000) 42:29-64.
Vandenbossche et al., "Host reaction against empty alginate-polylysine microcapsules. Influence of preparation procedure" *J. Pharm Pharmacol* (1993) 45:115-120.
Wang et al., "An encapsulation system for the immunoisolation of pancreatic islets" *Biotechnol* (1997) 15:358-362.
Wang et al., "Evaluation of sodium alginate for bone marrow cell tissue engineering" *Biomaterials* (2003) 24:3475-3481.
Wideroe et al., "Evaluation of the use of Sr2+ in alginate immobilization of cells" *Die Naturwissenschaften* (2001) 88:224-228.
Yang et al., "Calcium Alginate" *Cell Encapsulation Technology and Therapeutics* (1999) pp. 3-17.
Glicklis et al., In: Ikada Y. Okano T (eds.). "Biocompatible alginate scaffolds enabling prolonged hepatocyte functions in culture" Tissue Engineering for Therapeutic Use. Int. Congr.Ser. (1999) pp. 119-131.
International Search Report dated Mar. 11, 2005 for International Application No. PCT/US04/43681.

* cited by examiner

USE OF ALGINATE MATRICES TO CONTROL CELL GROWTH

CROSS REFERENCE TO RELATED APPLICATIONS

This application claims priority to provisional Application No. 60/531,917 which was filed Dec. 23, 2003 and which is incorporated herein be reference.

FIELD OF THE INVENTION

The present invention relates to alginate matrices and their uses in compositions and devices to inhibit cell proliferation. The present invention also relates to alginate formulations, constructs and devices having cell monolayers adhered thereto and their uses.

BACKGROUND OF THE INVENTION

Alginates are well known as versatile materials for cell encapsulation because of their ability to form highly biocompatible and strong gels under physiologic conditions at constant temperature (Skjåk-Bræk G, and T. Espevik Carbohydrates in Europe 1996; 14: 19-25; and Strand B L, et al. Minerva Biotecnologica 2000; 12: 223-233, which are incorporated herein be reference). Transplantation of alginate based tissue constructs may be useful in the treatment of a large number of diseases. Alginates can be used to entrap cells within microbeads, thus protecting the cells against immune attack from the host and physical stress. (Skjåk-Bræk G, and T. Espevik supra; Strand B L, et al supra; Yang H, et al. Cell Encapsulation Technology and Therapeutics. Boston, Birkhäuser, 1999: pp. 3-17; Uludag H, et al. Adv Drug Deliv Rev 2000; 42: 29-64; Orive G, et al. Nature Medicine 2003; 9: 104-107; Emerich D F and H C Salzberg Cell Transplant 2001; 10: 3-24; Sambanis A, Diabetes Technol Ther 2000; 2: 81-89 and Lanza R P, and D K Cooper. Molecular Medicine Today 1999; 4: 39-45, which are incorporated herein be reference.) Cells entrapped within alginate beads excreting therapeutic molecules may be used as implantable bioreactors in the treatment of a large variety of diseases, including cancer, diabetes, Parkinson's disease, chronic pain and liver failure (Emerich D F and H C Salzberg supra; Lanza R P, and D K Cooper supra; Wang T, et al. Nat Biotechnol 1997; 15: 358-362; Read T-A, et al. Nat Biotechnol 2001; 19: 29-34; Cai J, et al. Hepatology 2002; 36: 386-394; Canaple L, et al. Ann N Y Acad Sci 2001; 944: 350-361; Glicklis R, et al. In: Ikada Y, Okano T (Eds.). Tissue Engineering for Therapeutic Use. 1999: pp. 119-131; Emerich D F. Cell Transplant 2002; 11: 1-3; Emerich D F, et al. Neurosci Biobehav Rev 1992; 16: 437-447; Hagihara Y, et al. Cell Transplant 1997; 6: 527-530; Risbud M V and R R Bhonde J Biomater Sci Polymer Edn 2001; 12: 1243-1252, which are each incorporated herein by reference.) Therefore, alginates are now widely used as immobilizing materials for cells or tissue in the development of bioreactor systems for therapeutic use.

Alginates are also being studied as a biostructure materials in other types of medical applications. Dependent of the manufacturing process alginates may take various forms such as pastes, sponges, fibers, rods and tubes. Alginate sponges are being studied as materials for cell transplantation (Miralles G, et al. Journal of Biomedical Materials Research 2001; 57: 268-278; and Shapiro L and S. Cohen Biomaterials 1997; 18: 583-590, which are each incorporated herein by reference.) and nerve regeneration (Sufan W, et al. Journal of Neurotrauma 2001; 18: 329-338; Kataoka K, et al. J Biomed Mater Res 2001; 54: 373-384; and Hashimoto T, et al. Exp Brain Res 2002; 146: 356-368, which are each incorporated herein by reference.) Furthermore, alginate pastes containing chondrocytes have been injected into children as successful treatment of urethral reflux problems (Diamond D A and A A Caldamone J Urol 1999; 162: 1185-1188, which is incorporated herein by reference) and implants of chondrocytes in alginate gelled in situ by the addition of gelling solution directly into cartilage defects are promising (Fragonas E, et al. Biomaterials 2000; 21: 795-801, which is incorporated herein by reference.)

For applications involving cells in direct contact with the alginate structure, interactions between the cells and the alginate matrix may be crucial. In addition with respect to alginate bioreactor systems in particular, a major obstacle may be the selection and availability of sources of producer cells. As an alternative to processing fresh organs shortly prior to medical use, there are some advantages to growth of cells in vitro as an unlimited source for bioreactor production. Such cells can be genetically manipulated for better properties and the ability to produce therapeutic products.

Generally, for alginate entrapped proliferating cells, cell growth must in some way be controlled. It has been established that cell growth within the alginate gel matrix is dependent of the type of gel network (Constantinidis I, et al. Biomaterials 1999; 20: 2019-2027; and Stabler C, et al. Biomaterials 2001; 22: 1301-1310, which are each incorporated herein by reference), but the growth is also cell type dependent (Rokstad A M, et al. Cell Transplant 2002; 11: 313-324, which is incorporated herein by reference). Cells entrapped in weaker alginate gels containing a low content of guluronic acid have been shown to grow more rapidly as compared to cells entrapped in stronger i.e. high guluronic acid content gels (Constantinidis I, et al. supra; and Stabler C, et al. supra). As a result of cell growth and formation of colonies within the gel network, beads may disrupt and leakage of cells from the beads may occur (Constantinidis I, et al. supra; and Stabler C L, et al. Ann N Y Acad Sci 2002; 961: 130-133, which is incorporated herein by reference). Thus, a particular problem when using proliferating cells in alginate beads is that the cells continue to grow and proliferate, and the bead disruption and cell leakage that occurs exposes the cells to the immune system.

Animal cells are highly specialized in responding to and interacting with adjacent cells and extracellular matrixes. Such responses are controlled by specific genes. It has been demonstrated that collagen, a major normal extracellular matrix component, inhibits cells from entering into apoptosis and thereby provide a substrate for cell survival and differentiation (O'Connor S M, et al. Neurosci Lett 2001; 304: 189-193, which is incorporated herein by reference). The molecular mechanisms behind the interaction between cells and an alginate matrix are, however, unknown. While entrapped cells may form spheroid-like colonies within the gel network, it has also recently been demonstrated that cells may grow attached to alginate gel surfaces (Wang L, et al. Biomaterials 2003; 24: 3475-3481, which is incorporated herein by reference). It was established that rat bone marrow cells may grow on alginate gel surfaces in vitro without any chemical modification of the gel substrate (Wang L, et al. supra). In contrast to what was previously observed for cell growth within the alginate matrix, Wang et al also found a higher proliferation rate on gels of alginate with a high as compared to low content of guluronic acid. However, the lack of ability for C2C12 myoblasts to grow on non-chemically modified alginate surfaces has also been observed, while RGD peptide sequences bound to the alginate substrate allowed cell growth (Rowley J A et al. Journal of Biomedical Materials Research 2003; 60: 217-223; and Rowley J A, et al. Biomaterials 1999; 20: 45-53, which are incorporated herein by reference). These workers, however, also found best proliferation of myoblasts on alginate gels made with alginates containing a high content of guluronic acid.

Another common problem in applications involving implantation of alginate beads into in to animals is the growth of fibroblast and macrophages at the surface of selected beads (Vandenbossche G M R, et al. J Pharm Pharmacol 1993; 45: 115-120; Rokstad A M, et al. Ann N Y Acad Sci 2001; 944: 216-225; and Siebers U, et al. Journal of Molecular Medicine 1999; 77: 215-218, which are each incorporated herein by reference). This problem also occurs when other foreign bodies, such as devices, are implanted. Better knowledge about cell growth and attachment behavior in contact with the alginate matrix is therefore clearly needed.

There is a need to provide compositions comprising proliferating cells encapsulated in alginate and methods of using such compositions in which the growth and proliferation of the cells is controlled, thereby preventing bead disruption, cell leakage and the immune response that follows.

There is a need for compositions comprising cells encapsulated in alginate and methods of using such compositions wherein the cells excrete therapeutic molecules.

There is a need for compositions comprising cells encapsulated in alginate and methods of using such compositions in the treatment of diseases.

There is a need to provide implantable compositions and devices and methods of using such implantable compositions and devices in which the growth of unwanted host cells on the surface of such implantable compositions and devices is controlled.

SUMMARY OF THE INVENTION

The present invention relates to methods of inhibiting proliferation of a plurality of proliferating cells. The method comprises the step of maintaining the cells within an alginate matrix that comprises alginate polymers and Strontium.

The present invention also relates methods of inhibiting cell growth on a composition in a human body. The methods comprise the step of maintaining the composition in the human's body. The composition comprises an alginate gel comprising Strontium.

The present invention also relates methods of inhibiting cell growth on a composition in an animal for 180 or more days. The methods comprise the step of maintaining the composition in the animal's body for 180 or more days. The composition comprises an alginate gel comprising Strontium.

The present invention also relates to methods of inhibiting cell growth on a device in an animal. The methods comprise the step of maintaining the device in the animal. The device comprises an alginate gel comprising Strontium.

The present invention also relates to devices that have on their exterior surface an alginate matrix that comprises Strontium.

The present invention relates to a method of coating or covering the exterior surface of a cell free composition or device with an alginate matrix. The method comprises the step of first covering or coating the cell free composition or device or a component thereof, with an alginate solution, and successively or subsequently applying by immersion, submersion, spraying, atomization or other technique, a divalent cross-linking ion whereby the alginate polymers of the alginate solution coating the device become cross-linked by the divalent cross linking ions and an alginate matrix coating the device is formed.

The present invention also relates to compositions comprising an alginate body that comprises a single layer of cells coating the exterior surface of the alginate body. The alginate body comprises one or more of Calcium, Barium, Zinc and Copper.

The present invention also relates to sheets of alginate that comprise a single layer of cells on the surface. The alginate sheets comprise one or more of Calcium, Barium, Zinc or Copper.

The present invention also relates to methods of preparing an artificial tissue. The methods comprise growing a plurality of sheets of cells, the sheets of cells each comprising a single layer of cells on a sheet comprising an alginate matrix that comprises alginate polymer and one or more of Calcium, Barium, Zinc or Copper, stacking the sheets of cells by placing the bottom of one sheet of cells on the cells of a another sheet of cells and maintaining stacked sheets of cells under conditions in which the alginate matrix of each sheet is dissolved whereby each single layer of cells comes in direct contact with at least one other single layer of cells to produce a tissue having a plurality of layers of cells.

DETAILED DESCRIPTION OF PREFERRED EMBODIMENTS

Figure 1:
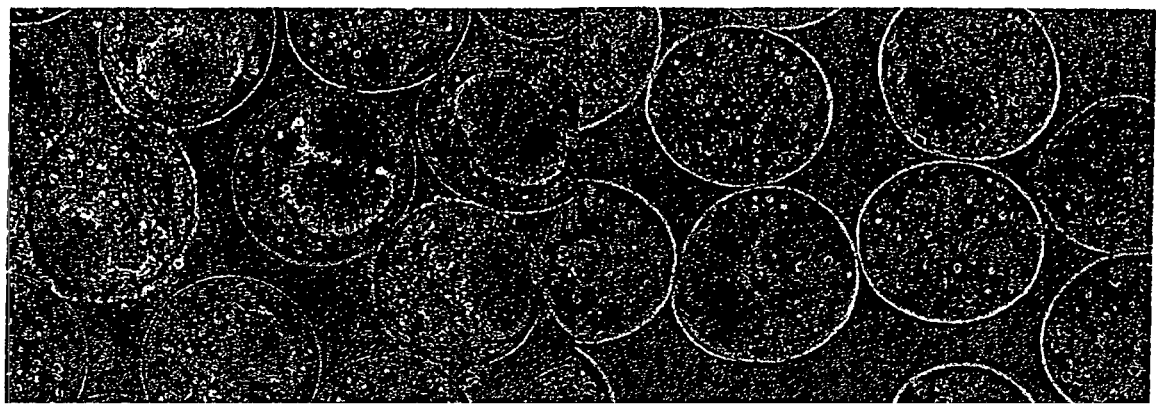
FIG. 1 shows a light microscopic image of HEK 293 Endo cells encapsulated in calcium (left) and strontium (right) alginate beads for about 1.5 months.

The present invention arises out of discoveries that demonstrate that the type of divalent cation used to produce an alginate matrix has an effect on the proliferation of cells that come in contact with such alginate matrix. These discoveries allow for the design and production of specific compositions and devices that include specific types of alginate matrices based upon the desire to inhibit or support cell proliferation. Some aspects of the present invention provide compositions and devices and uses thereof which are associated with alginate matrices that inhibit cell proliferation. Some aspects of the present invention provide compositions and devices and uses thereof which are associated with alginate matrices that promote controlled cell growth whereby cells can be grown and maintained as a single monolayers of cells.

According to some embodiments of the aspect of the invention involving inhibition of cell proliferation, the proliferation of cells encapsulated within an alginate matrix can be inhibited in order to prevent problems that are associated with maintaining proliferating cells within an alginate matrix, particularly the problems that arise when such alginate matrix-encapsulated proliferating cells are implanted in an animal. Similarly, cell proliferation can be inhibited to prevent overgrowth of an implant by the recipient's own cells over implanted compositions and devices that remain in the body of a recipient for extended periods of time. Inhibition of cell overgrowth overcomes problems associated with the use of implantable compositions and devices and provides for improved compositions, devices and methods.

It has been discovered that the presence of Strontium in alginate matrices inhibits cell proliferation without affecting cell viability. This discovery provides for methods of inhibiting proliferation of proliferating cells within such matrices for surprisingly long periods of time, and for methods of inhibiting cell proliferation to prevent cell overgrowth over implanted compositions and devices so that such compositions and devices can be maintained in the body of the recipient for surprisingly long periods of time.

In the case of implantable compositions in which cells intended to secrete material into a recipient's body are encapsulated in an alginate matrix, the presence of Strontium inhibits the overgrowth of cells from the recipient's body which if present can prevent material from being secreted from the compositions into the body of the recipient. By preventing the overgrowth, the secretion from the composition can continue unimpeded over time.

The prevention of cell overgrowth in compositions comprising living cells encapsulated in an alginate matrix also allows the cells within the matrix continued access to nutrients and materials necessary for continued viability for surprising long periods in time.

In embodiments in which the composition is an alginate matrix encapsulating proliferating cells, the presence of the Strontium inhibits the proliferation of the encapsulated cells, which is known to cause many problems that prevent the long-term use of such compositions. As used herein, "proliferating cells" is meant to refer to cells that are capable of continuous and repeated cell division under the conditions in which they are maintained in the absence of Strontium that is present at a level effective to inhibit cell proliferation. Inhibition of continued cell proliferation prevents disruption of the matrix integrity and the subsequent leakage of the cells into the body. Accordingly, some embodiments of the invention provide methods that allow compositions containing proliferating cells to be maintained in the body of the recipient for surprising long periods of time without matrix disruption and cell leakage.

The inhibition of cell proliferation by alginate matrices containing Strontium allows for methods of inhibiting cell overgrowth over implanted devices and compositions, thereby overcoming problems associated with the use of implanted devices and compositions. Improved devices and improved methods of using the devices are provided. Improved devices, such as those having Strontium containing alginate matrices on exterior surfaces and methods of using such compositions are provided. These devices are particularly useful because their use is characterized by an inhibition of cell overgrowth associated with many implanted devices and the problems and undesirable results of such cell overgrowth. Improved compositions include those which comprise cells encapsulated within an alginate matrix as described above as well as cell-free compositions such as those comprising or consisting of alginate matrices and methods of using such compositions are also provided. In some embodiments, compositions comprise an alginate matrix that encapsulates a drug or protein that is secreted from the implanted compositions into the body. In some embodiments, compositions may be used as bulking agents which can be used, for example, to provide a biocompatible material that can occupy space when needed to support, encase or become integrated with devices and tissues.

According to some embodiments of the present invention, methods of inhibiting proliferation of a plurality of proliferating cells are provided. The methods comprise the step of maintaining the proliferating cells within an alginate matrix that comprises alginate polymers and Strontium. In some preferred embodiments, the encapsulated cells are maintained within the body of an animal. In some embodiments, the animal is a mammal, preferably a human, a rodent such as a mouse or a rat, or a bovine, ovine, equine, canine or feline species. In some embodiments, the animal is a fish or an avian species. In some embodiments, the cells are maintained within the alginate matrix for at least 7 days, preferably at least 30 days, in some embodiments at least 60 days, in some embodiments at least 90 days, more preferably at least 180 days and more preferably one year or more. In preferred embodiments, the cells within the alginate matrix are maintained in the body of an animal for at least 7 days, preferably at least 30 days, in some embodiments at least 60 days, in some embodiments at least 90 days, more preferably at least 180 days and more preferably one year or more. In some embodiments, the cells within the alginate matrix are maintained within an implantable device such as a container that can be maintained in the body of an animal. In some embodiments, the cells within the alginate matrix that are maintained within an implantable device can be maintained for at least 7 days, preferably at least 30 days, in some embodiments at least 60 days, in some embodiments at least 90 days, more preferably at least 180 days and more preferably one year or more. In some embodiments, the proliferating cells within the alginate matrix are attached as a monolayer to the exterior surface of an alginate body encapsulated within the alginate matrix. In some embodiments, that alginate body comprises alginate polymers and Calcium. In some embodiments, that alginate body comprises alginate polymers and one or more of Calcium, Barium, Zinc and Copper.

According to some embodiments of the present invention, methods of inhibiting cell growth on the exterior surface a composition that comprises a plurality of cells in a human's body for seven or more days. The method comprises the step of maintaining the composition in the human's body for seven or more days wherein the composition comprises a plurality of cells encapsulated in an alginate matrix comprising Strontium. The cells may be proliferating cells, non-proliferating cells or a combination of both. In some embodiments, the composition is maintained in the body of a human for one year or more.

According to some embodiments of the present invention, methods of inhibiting cell growth on the exterior surface a composition that comprises a plurality of cells in an animal's body for at least 180 days. The method comprises the step of maintaining the composition in the animal's body for seven or more days wherein the composition comprises a plurality of cells encapsulated in an alginate matrix comprising Strontium. The cells may be proliferating cells, non-proliferating cells or a combination of both. In some embodiments, the composition is maintained in the body of an animal for one year or more.

In some embodiments in which cells are encapsulated within alginate matrices, the matrices are generally spheroid. In some embodiments, the matrices are irregular shaped. Generally, the alginate matrix must be large enough to accommodate an effective number of cells while being small enough such that the surface area of the exterior surface of the matrix is large enough relative to the volume within the matrix. As used herein, the size of the alginate matrix is generally presented for those matrices that are essentially spheroid and the size is expressed as the largest cross section measurement. In the case of a spherical matrix, such a cross-sectional measurement would be the diameter. In some embodiments, the alginate matrix is spheroid and its size is between about 20 and about 1000 µm. In some embodiments, the size of the alginate matrix is less than 100 µm, e.g. between 20 to 100 µm; in some embodiments, the size of the alginate matrix is greater than 800 µm, e.g. between 800-1000 µm. In some embodiments, the size of the alginate matrix is about 100 µm, in some embodiments, the size of the alginate matrix is about 200 µm, in some embodiments, the size of the alginate matrix is about 300 µm; in some embodiments, the size of the alginate matrix is about 400 µm, in some embodiments, the size of the alginate matrix is about 500 µm; in some embodiments, the size of the alginate matrix is about 600 µm; and in some embodiments about 700 µm.

In some embodiments in which cells are encapsulated within an alginate matrix, encapsulated cells are mammalian cells, preferably human cells. In some embodiments in which encapsulated cells are non-proliferating cells, the non-proliferating cells may be selected from the group consisting of, but not limited to: pancreatic islets, hepatic cells, neural cells, renal cortex cells, vascular endothelial cells, thyroid and parathyroid cells, adrenal cells, thymic cells, ovarian cells, and other cell types of primary origin. In some embodiments in which encapsulated cells are proliferating cells, the proliferating cells may derived from established cell lines, such as, but not limited to, for example, 293, MDCK and C2C12 cell lines. In some embodiments, encapsulated cells comprise an expression vector that encodes one or more proteins that are expressed when the cells are maintained. In some embodiments, the protein is a cytokine, a growth factor, insulin or an angiogenesis inhibitor such as angiostatin or endostatin. Proteins with a lower molecular weight, less than about 60-70 kD, are particularly good candidates because of the porosity of the gel-network. In some embodiments, the encapsulated cells are attached as a monolayer to the exterior surface of an alginate body encapsulated within the alginate matrix. In some embodiments, that alginate body comprises alginate polymers and Calcium.

According to some embodiments of the present invention, methods of inhibiting cell growth on the exterior surface a cell-free composition in an animal's body for seven or more days are provided. The method comprises the step of maintaining the cell-free composition in the animal's body wherein the composition comprises an alginate matrix comprising Strontium. In some embodiments, the cell-free composition comprises a drug encapsulated within the alginate matrix. In some embodiments, the cell-free composition comprises a protein encapsulated within the alginate matrix. In some embodiments, the cell-free composition is a tissue bulking implant. In some embodiments, the cell-free composition is a tissue bulking implant that consists essentially of alginate polymers and Strontium.

According to some embodiments of the present invention, methods of inhibiting cell growth on the exterior surface a device in an animal's body are provided. The method comprises the step of maintaining the device in the animal's body wherein an alginate matrix comprising Strontium is deposited on the exterior surface the device. In some embodiments, the device is selected from the group consisting of: a stent, a cardiac pacemaker, a catheter, an implantable prosthetic, a surgical screw, a surgical wire, a tissue bulking implant, an esophagus reflux inhibiting implant, an incontinence inhibiting implant, a renal reflux inhibiting implant, a container suitable for holding cells that are deposited on the exterior of a surface and/or encapsulated with an alginate matrix such as a solid device or macrocapsule, a breast implant, a chin implant, a cheek implant, a pectoral implant, a gluteus implant and a dental implant.

In some preferred embodiments, the cell-free compositions or devices are maintained within the body of a mammal, preferably a human, a rodent such as a mouse or a rat, or a bovine, ovine, equine, canine or feline species. In some embodiments, the animal is a fish or an avian species. In some embodiments, the device is maintained in the body of an animal for at least 7 days, preferably at least 30 days, more preferably at least 60 days, more preferably at least 90 days, more preferably at least 180 days and more preferably one year or more.

The present invention also relates to implantable devices having an alginate matrix comprising Strontium deposited on the exterior surface. In some embodiments, the device is selected from the group consisting of: a stent, a cardiac pacemaker, a catheter, a prosthetic, a surgical screw, a surgical wire, a tissue bulking implant, an esophagus reflux inhibiting implant, an incontinence inhibiting implant, a renal reflux implant, a container suitable for holding cells that are deposited on the exterior of a surface and/or encapsulated with an alginate matrix such as a solid device or macrocapsule, a breast implant, a chin implant, a cheek implant, a pectoral implant, a gluteus implant and a dental implant.

The present invention relates to a method of coating or covering the exterior surface of a cell free composition or device with an alginate matrix comprising the step of first covering or coating the cell free composition or device or a component thereof, with an alginate solution, and successively or subsequently applying by immersion, submersion, spraying, atomization or other technique, a divalent cross-linking ion such as Calcium, Barium, Copper, Zinc or Strontium whereby the alginate polymers of the alginate solution coating the device become cross-linked by the divalent cross linking ions and an alginate matrix coating the device is formed thereby. In such embodiments, the alginate solution used for the initial coating or covering would be of sufficient viscosity to effectively coat or cover the cell free composition or device. In some embodiments, the initial covering or coating is further cross-linked in the hydrated (wet) state. In some embodiments, the initial covering or coating is first dried before reaction with the cross-linking ion.

These various aspects of the invention involving inhibition of cell proliferation each provide alginate matrices comprising Strontium. In some embodiments, the alginate matrix is initially essentially free of one or more of Calcium, Barium, Zinc and Copper. In some preferred embodiments, the divalent cations in the alginate matrix consist of Strontium. In some preferred embodiments, the alginate matrix consists essentially of alginate polymers and Strontium. In some embodiments, the alginate polymers of the alginate matrix contain more than 50% α-L-guluronic acid. In some embodiments, the alginate polymers of the alginate matrix contain more than 60% α-L-guluronic acid. In some embodiments, the alginate polymers of the alginate matrix contain 60% to 80% α-L-guluronic acid. In some embodiments, the alginate polymers of the alginate matrix contain 65% to 75% α-L-guluronic acid. In some embodiments, the alginate polymers of the alginate matrix contain more than 70% α-L-guluronic acid. In some embodiments, the alginate polymers of the alginate matrix have an average molecule weight of from 20 to 500 kD. In some embodiments, the alginate polymers of the alginate matrix have an average molecule weight of from 50 to 500 kD. In some embodiments, the alginate polymers of the alginate matrix have an average molecule weight of from 100 to 500 kD. In some embodiments, the alginate matrix is free of polycationic amino acids.

It has been discovered that cells adhered to the surface of alginate matrices can be maintained as a monolayer using alginate matrices that comprise one more of Calcium, Zinc and Barium. This discovery provides aspects of the invention which relate to alginate bodies made up of alginate matrices and sheets of alginate matrices having monolayers of cells adhered to their surfaces and to methods of using such alginate bodies and alginate sheets. It has been discovered that cells adhered to such alginate bodies and alginate sheets may be maintained in a stable form as monolayers. Alginate bodies and alginate sheets provide a stable platform on which to maintain, propagate and handle cells. Alginate bodies and alginate sheets can comprise a plurality of non-proliferating cells adhered to the surfaces as a monolayer, allowing for ease of handling, efficient maintenance, more regular dispersal in a volume, and prevention of clumping of such cells. Furthermore, such alginate bodies and alginate sheets may be used to keep the cells at a very high density, still allowing the exchange of nutrients keeping the cells viable, and thereby increase the excretion efficiency of therapeutic products. Growing and maintaining monolayers of cells on alginate surfaces is useful to provide specific shapes of cell/matrix compositions. In addition, by growing the cells as monolayers, the cells can be arranged in an optimal way to allow the cells to remain viable at very high concentrations. In some embodiments, the cells are incorporated or otherwise used in connection with devices or macrocapsules. By maintaining cells as a monolayer on an alginate surface, the cells can be more optimally arranged within the device or macrocapsule. This can be particularly useful in such devices where the volume is small and optimization of cell density is critical.

Alginate bodies and alginate sheets that comprise a plurality of proliferating cells have the same advantages as those with non-proliferating cells with the additional advantage of allowing for more controlled propagation of cells as a monolayer.

In some embodiments, compositions comprise an alginate body that comprises a single layer of cells on the exterior surface of the alginate body, wherein the alginate body comprises one or more of Calcium, Barium, Zinc and Copper. In some embodiments, the alginate body is generally spheroid in shape and size of the alginate body is between less than 600 μm, in some embodiments less than 500 μm, in some embodiments less than 400 μm, in some embodiments less than 300 μm, in some embodiments less than 200 μm and in some embodiments less than 100 μm.

In some embodiments the cells are mammalian cells, preferably human cells. In embodiments, cells are non-proliferating cells, preferably cells selected from the group consisting of, but not limited to: stem cells, pancreatic islets, hepatic cells, neural cells, renal cortex cells, vascular endothelial cells, thyroid and parathyroid cells, adrenal cells, thymic cells, and ovarian cells. In some embodiments, the cells are proliferating cells such as cells derived from established cell lines, for example, HEK 293, MDCK and C2C12 cell lines. In some embodiments, the cells comprise an expression vector that encodes a protein that is expressed when the cells are maintained. In some embodiments, the protein is a cytokine, a growth factor, insulin or an angiogenesis inhibitor such as angiostatin or endostatin.

In some embodiments, that alginate body is encapsulated within an alginate matrix such as an alginate matrix comprising alginate polymers and Strontium. In some embodiments, the monolayer is grown using proliferating cells that are then converted to into terminally differentiated or other non-proliferating state. In some embodiments, the alginate bodies with monolayers of cells adhered thereto are contained within an implantable device.

In some embodiments of the invention, encapsulated cells that are contained within an alginate matrix that comprises alginate polymers and Strontium are incorporated into an implantable device which is optionally coated within an alginate matrix that comprises alginate polymers and Strontium. In some such embodiments, the cells within the alginate matrix are attached as a monolayer to the exterior surface of an alginate body which preferably comprises alginate polymers and Calcium, Barium, Zinc, Copper and/or Magnesium. Cells used in such embodiments are preferably cells selected from the group consisting of: stem cells, pancreatic islets, hepatic cells, neural cells, renal cortex cells, vascular endothelial cells, thyroid and parathyroid cells, adrenal cells, thymic cells, ovarian cells, HEK 293 cells, MDCK cells and C2C12 cell. In some embodiments, the cells comprise an expression vector that encodes a protein, such as for example a cytokine, a growth factor, insulin or an angiogenesis inhibitor such as angiostatin or endostatin, that is expressed when the cells are maintained.

In some embodiments of the invention, an implantable device comprising encapsulated insulin producing cells, such as pancreatic islet cells, that are contained within an alginate matrix that comprises alginate polymers and Strontium are used to treat individuals suffering from diabetes. The device, which allows for the transfer of materials between its inside and outside is implanted and maintained in the individual and the cells within the device produce and release insulin which travels into the individual's body. In some such embodiments, the implantable device is coated with an alginate matrix that comprises alginate polymers and Strontium. In some such embodiments, the insulin producing cells that are contained within an alginate matrix are attached as a monolayer to the exterior surface of an alginate body which preferably comprises alginate polymers and Calcium, Barium, Zinc, Copper and/or Magnesium.

In some embodiments, compositions comprise an alginate sheet that comprises a single layer of cells on the surface of the alginate sheet, wherein the alginate sheet comprises Calcium. In some embodiments the cells are mammalian cells, preferably human cells. In embodiments, cells are non-proliferating cells, preferably cells selected from the group consisting of, but not limited to: stem cells, pancreatic islets, hepatic cells, neural cells, renal cortex cells, vascular endothelial cells, thyroid and parathyroid cells, adrenal cells, thymic cells, and ovarian cells. In some embodiments, the cells are proliferating cells such as cells derived from established cell lines, for example, but not limited to, HEK 293, MDCK and C2C12 cell lines. In some embodiments, the cells comprise an expression vector that encodes one ore more proteins that are expressed when the cells are maintained. In some embodiments, methods are provided of preparing an artificial tissue. A plurality of sheets of cells are grown in which the sheets of cells each comprising a single layer of cells on a sheet comprising an alginate matrix that comprises alginate polymer and Calcium. The sheets of cells are stacked by placing the bottom of one sheet of cells on the top of another sheet of cells. The stacked sheets of cells are maintained under conditions in which the alginate matrix of each sheet is dissolved whereby each single layer of cells comes in direct contact with at least one other single layer of cells to produce a tissue having a plurality of layers of cells. In some embodiments, the plurality of sheets of cells comprises a plurality of sheets of epithelial cells. In some embodiments, the plurality of sheets of cells further comprises one or more sheets of fibroblast cells. In some embodiments, the plurality of sheets of cells comprises a plurality of sheets of hepatocytes. In some embodiments, the plurality of sheets of cells comprises one or more sheets of islet cells. In some embodiments, the cells used are stem cells. According to some embodiments, epithelial tissue is constructed as artificial skin. Layers of epithelial cells (keratinocytes and others) are added to layers of connective tissue (fibroblasts) to be used for replacement of damaged skin in patients.

These various aspects of the invention involving maintaining cells as a monolayer on a alginate body or sheet provide alginate matrices comprising one or more of Calcium, Barium, Zinc and Copper. In some embodiments, the alginate matrix is essentially free of Strontium. In some preferred embodiments, the divalent cations in the alginate matrix consist of Calcium. In some preferred embodiments, the alginate matrix consists essentially of alginate polymers and Calcium. In some embodiments, the alginate polymers of the alginate matrix are greater than 50% α-L-guluronic acid monomers. In some embodiments, the alginate polymers of the alginate matrix contain more than 60% α-L-guluronic acid. In some embodiments, the alginate polymers of the alginate matrix are between 60% and 80% α-L-guluronic acid. In some embodiments, the alginate polymers of the alginate matrix contain more than 70% α-L-guluronic acid. In some embodiments, the alginate polymers of the alginate matrix contain between 65% and 75% α-L-guluronic acid. In some embodiments, the alginate polymers of the alginate matrix have an average molecule weight of from 20 to 500 kD. In some embodiments, the alginate polymers of the alginate matrix have an average molecule weight of from 50 to 500 kD. In some embodiments, the alginate polymers of the alginate matrix have an average molecule weight of from 100 to 500 kD. In some embodiments, the alginate matrix is free of polycationic amino acids.

EXAMPLES

Example 1

In this work we have studied cell cultures entrapped in alginate beads and observed their growth within the beads and on the bead surface during time. We have found that cell growth may occur on the bead surface and that cells may cover the beads as spherical monolayers, and furthermore that this process is gelling ion dependent. These observations may have implications for understanding the mechanisms behind interactions between cells and the alginate matrix.

Materials and Methods

Cell Cultures and Encapsulation Procedure

Human HEK 293 Endo cells (embryonic kidney cells, transfected for endostatin production) and canine MDCK cells (derived from an apparently normal kidney of an adult female cocker spaniel) were used. The cells were routinely grown as monolayer cell cultures and recultured three times a week. In each experiment the cells were trypsinized, mixed with 1.8% PRONOVA SLG 20 alginate solutions and entrapped in alginate beads by using an electrostatic bead generator as previously described in Klokk T I, and J E Melvik, J Microencapsulation 2002; 19: 415-424, which is incorporated herein by reference. Beads with a size of about 400 μm were made by using an 0.35 mm outer diameter nozzle and operating the bead generator at an electrostatic potential of about 6 kV/cm with a distance between nozzle tip and gelling bath of about 1 cm. The presence of sodium ions during gelling was avoided as much as possible by using mannitol as the osmolyte in order to obtain inhomogeneous beads with better properties (Strand B L, et al. Biotechnol Bioeng 2003; 82: 386-394, which is incorporated herein by reference). The gelling solutions used contained 50 mM $CaCl_2$, SrCl2 or BaCl2. After gelling the beads were transferred into cell culture flasks and added normal cell growth medium. The growth medium was changed 2-3 times each week, and the beads was also regularly transferred into new flasks in order to avoid extensive growth of cells released from the beads on the flask growth surface. The beads and cell growth were followed with time by using light or fluorescence microscopy.

Live Dead Staining of Entrapped Cells

Detection of live and dead cells was performed by using a LIVE/DEAD Viability/Cytotoxicity Kit (Molecular Probes, Oregon, USA). Staining of cells was performed as described in the procedure following the kit. Green fluorescence is detected from intracellular esterase-converted calcein as an indicator of living cells whereas red fluorescence is detected from simultaneous ethidium staining of dead cells (leaking cell membrane). Alginate bead containing cells were observed by confocal imaging microscopy.

Results

Human HEK 293 Endo cells and canine MDCK cells were encapsulated in calcium and strontium alginate beads without any coating material and observed visually under light microscopy during time. The growth behavior of the two cell lines was clearly different. After only a few days cell growth could be observed inside the beads and this was clearly more pronounced for the HEK 293 Endo cells. Large cell aggregates developed within the beads and after less than a month cell growth outside of the beads could be seen. FIG. 1 shows images of HEK 293 Endo cells after 1.5 months in culture in both strontium and calcium alginate beads. Proliferation of cells within the beads was clearly dependent of the gelling ion as the cell load within the beads was less with strontium ions. In both cultures leakages of cells occurred as cell colonies attached to the bottom of the culture flasks and gave rise to colonies there. However, for calcium alginate beads, cells were also able to grow at the surface of some of the beads and cell aggregates more or less loosely attached to the beads could also be seen. No such cell overgrowth, however, was seen on strontium alginate beads.

Figure 2:
FIG. 2 shows light microscopic images of MDCK cells entrapped in calcium (left) and strontium (right) alginate beads after about 2.5 months in culture. All calcium alginate beads are completely covered with attached cells. For strontium alginate beads, single cells and aggregates of cells can be seen within the beads.

For MDCK cells entrapped in alginate beads the proliferation rate was considerably slower than for the HEK 293 Endo cells. In this experiment (FIG. 2) cells at a concentration of $2 \times 10^6$ cells/ml were entrapped in 350 μm beads of either strontium or calcium alginate. Cell growth could be seen within both types of beads after some days and this was more pronounced for the calcium beads. Some MDCK cells also escaped from both bead types and gave rise to colonies at the surface of the culture flasks. Also for these cells there was a major difference in the growth of cells at the bead surface between calcium and strontium alginate beads. In FIG. 2 is shown images of two alginate gel beads containing MDCK cells after about 2.5 months in culture. At this stage all calcium alginate beads were completely covered with cells while none of the strontium beads did show any overgrowth of cells. The growth behavior at the bead surface was clearly different between the two cell types as MDCK cells covered the cells as monolayers at the calcium bead surface in contrast to the HEK 293 Endo cells where cells were also growing as large aggregates more or less loosely attached to the bead surface.

Figure 3:
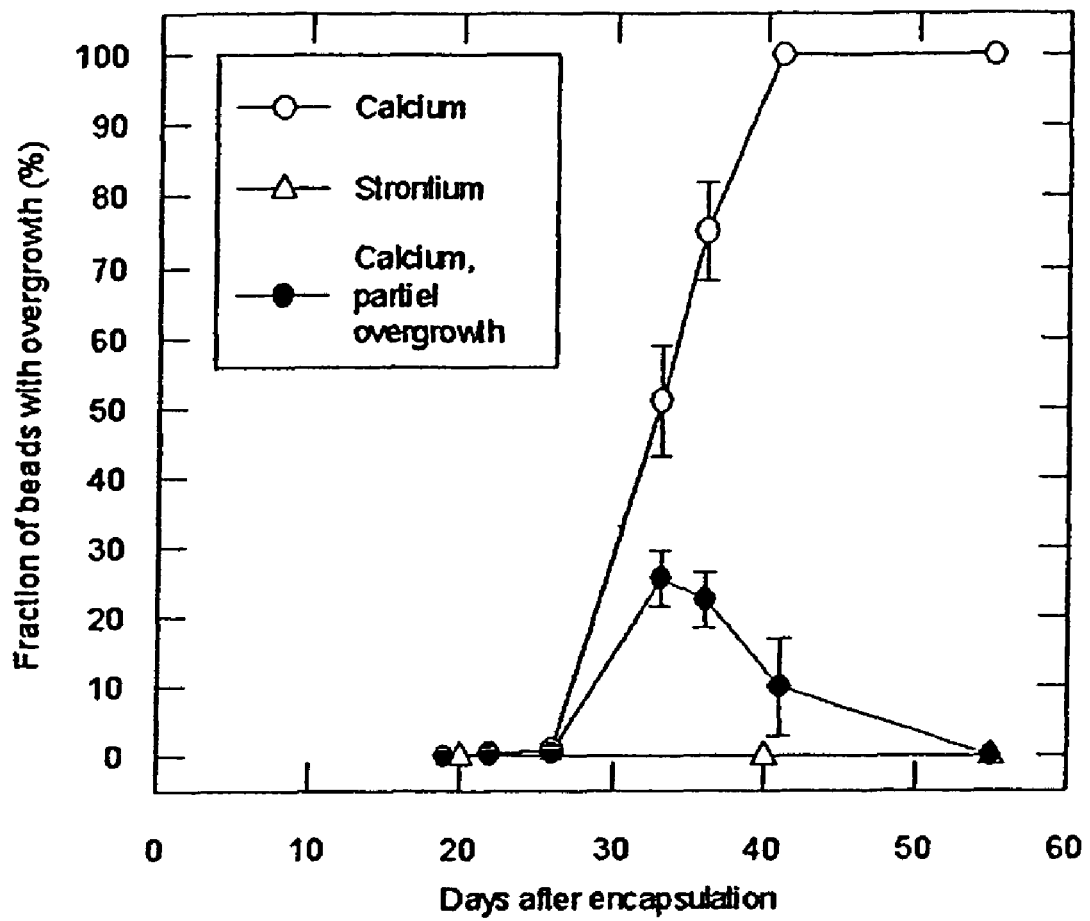
FIG. 3 is a graph showing fractions of beads with MDCK cell overgrowth as a function of time after encapsulation in Calcium or Strontium alginate beads. The number of calcium alginate beads with incomplete overgrowth was also counted.

The overgrowth of cells on the beads could easily be observed in the light microscope. By counting a limited number of beads the growth pattern for the cells at the bead surface was characterized (FIG. 3). It was also noted whether the beads were completely or only partly covered with cells. As can be seen in FIG. 3 cell growth on calcium alginate beads occurred after about 3 weeks and the fraction of beads with attached cells increased rapidly until all beads were covered with cells about 40 days after encapsulation. During the experiment only a up to about 25% of calcium alginate beads were incompletely covered with cells at a time. This was consistent with a rapid cell overgrowth as soon as growth at the bead surface was initiated. We have in separate experiments observed the beads for more than five months. It was observed that the calcium alginate beads were still covered with complete spherical monolayer of MDCK cells while none of the strontium beads displayed any cell growth at the surface.

We also tested whether cells from beads covered with cells were able to transfer and attach to empty beads by adding new empty beads to the cell culture. The beads were observed for several weeks without any indication of cell transmission to the new beads (picture not shown).

The growth of cells within and at the bead surface was also studied by "live/dead" staining of the cells and confocal imaging techniques. In this experiment green fluorescence is emitted from intracellular esterase-converted calcein in living cells whereas red fluorescence is from ethidium staining of dead cells (leaking cell membrane). Confocal fluorescence images were shown as sections throughout the beads. Thus, only a fraction of the fluorescent cells within the beads were shown in the images (pictures not shown). For the calcium alginate beads a spherical monolayer of viable cells are clearly seen while cells in the center of the beads are dead. The reason for the necrosis within the bead is likely explained by depletion of oxygen and other nutrients as a result of consumption from the spherical monolayer of cells. In contrast the strontium alginate bead were not covered with cells and contained viable cells. However, it should be noted that large colonies of cells within strontium beads with time also gave rise to cell aggregates with necrotic centers.

Discussion

Well-defined medical grades of alginates which have a very low level of impurities (Dornish J M, et al. Ann NY Acad Sci 2001; 944: 388-397 and Skaugrud Ø, et al. Biotechnol Genet Eng Rev 1999; 16: 23-40, which are each incorporated herein by reference) were used. It is therefore very unlikely that endotoxins or other impurities, which are commonly present in higher or unknown quantities of most commodity alginates, may have had any influence on the observations made (Skaugrud Ø, et al. supra).

The growth pattern of cells within the alginate gel network was clearly different between the two cell lines (FIGS. 1 and 2). Although the MDCK cells showed a more rapid growth in monolayer cultures, the growth within the gel network was slower as compared to the HEK 293 Endo cells. Similar differences have previously also been reported (Rokstad A M, et al. supra). The higher strength of the Strontium gel network, however, maintained bead integrity with both of the encapsulated cell lines for a longer time as compared to Calcium beads. The strength of the alginate network microstructure is likely to directly influence the growth rate of the cells (Rokstad A M, et al. supra and Stabler C L and A Sambanis supra). The strength of the gel network may also change with time as a result of cell proliferation but also as a result of ion exchange between the gel and the growth medium (Rokstad A M, et al. supra; Smidsrød O and G Skjåk-Bræk. TIBTECH 1990; 8: 71-78; and Read T-A, et al. Int J Devl Neuroscience 1999; 17: 653-663, which are each incorporated herein by reference). The presence of enzymatic mechanisms for degradation of the gel network has also been suggested (Rokstad A M, et al. supra). Compared to the Calcium alginate gel a Strontium alginate gel will be less susceptible to degradation during time in a solution with low concentration of gelling ions. The release of cells from the different beads is likely to occur as a result of disruption of some of the beads but also as a result of cell growth and movement through the gel network.

The growth pattern of cells at the bead surface was also highly different between the two cell lines. While the HEK 293 Endo cells were growing more or less attached to the beads (FIG. 1), MDCK-cells covered the beads as a complete spherical monolayer (FIG. 2). Clearly the MDCK-cells were strongly attached to the calcium alginate bead surface as demonstrated by confocal imaging. The tight attachment to the calcium bead surface suggests an anchorage dependent growth involving specific attachment mechanisms. Furthermore, the lack of growth at the Strontium gel surface suggests that the presence of specific gelling ions within the gel network is crucial. This may be directly related to the presence of the gelling ions alone or differences in the gel structure. The significance of the gelling ions is supported by Attramdal A. Journal of Peridontal Research 1969; 4: 281-285, which is incorporated herein by reference, who observed that Strontium ions in contrast to Calcium ions did not support the attachment of cells to a glass surface. It is now also well known that normal cell attachment to extracellular matrices or cells are dependent upon membrane proteins like integrins and cadherins. Furthermore, such cell membrane attachment proteins are also known to be dependent of divalent cations for substrate attachment (Hynes R O. Cell 2002; 110: 673-687, which is incorporated herein by reference). While not wishing to limit the invention to any particular theory, it is a plausible explanation that divalent ion dependent anchorage mechanisms are involved in the attachment of the cells to the Calcium gel surface. Although the chemical properties of the Strontium ions are similar to those of Calcium ions, cell attachment mechanisms may not be supported by the Strontium gel network. After more than five months, no attached cells were observed on the strontium beads while viable cells were still covering all the calcium beads completely.

The outgrowth of MDCK cells on the calcium alginate bead surface started after about 3 weeks (FIG. 3). This relatively long initiation time without any growth on the bead surface is surprising. Also, the growth period on the bead surface is short as reflected by the low fraction of beads with partial overgrowth. This suggests some initiation mechanism and a rapid growth rate on the bead surface. The explanation for these observations could possibly involve some cellular adaptation mechanisms, but possibly also be related to changes in the gel network as a result of Calcium release (Smidsrød O and G. Skjåk-Bræk supra). The observation that beads covered with cells did not transfer cells to the surface of the empty beads indicates that some disruption in the surface of the gel or strong initial contact between the cell and gel surface is necessary in order to allow growth initiation.

Growth on alginate surfaces has also been reported by Wang et al. supra who found a better growth on alginate with a high as compared to low guluronic acid content. It was suggested that differences in the gel structure and strength between the two types of gels could explain the difference. Similar results has also been reported for RGD modified alginate (Rowley J A and D J Mooney D J supra). Better growth on a high guluronic acid content alginate content alginate compared to low guluronic acid content alginate may also be influenced by the fact that a higher content of Calcium present in the high guluronic acid alginate gel network may promote better cell attachment and stronger growth. (Preliminary observations also shows a more rapid growth of HEK 293 Endo cells on alginate beads made from a high guluronic acid content alginate as compared to a low guluronic acid content alginate. Growth of fibroblasts and macrophages on the surface of empty alginate beads implanted in animals has commonly been observed (Vandenbossche G M R, et al. supra; Rokstad A M, et al (2001) supra; Siebers U, et al. supra). The host response towards implanted beads may in some cases rather be the effect of the alginate surface as a growth substrate for cells from the host, rather than initiation of adverse immunologic related reactions towards the beads. Use of Strontium as a gelling ion in alginate gels would then give an advantage in order to avoid cell overgrowth. The use of Strontium has previously been suggested in encapsulation applications because of good biocompatibility and higher gel strength (Wideroe H and S Danielsen. Die Naturwissenschaften 2001; 88: 224-228.44, which is incorporated herein by reference) and the data herein showing Strontium inhibiting cell proliferation provides additional unexpected benefits when using this gelling ion. Live/dead analysis of Strontium beads clearly showed the presence of viable cells within the beads after months in culture.

The growth of cells on alginate surfaces holds an interesting potential in applications as a scaffold material supporting cell growth (Wang L, supra; Alsberg E, et al. Proc Natl Acad Sci USA 2002; 99: 12025-12030; and Loebsack A, et al. Journal of Biomedical Materials Research 2001; 57: 575-581, which are each incorporated herein by reference). The growth of cells as monolayers on alginate surfaces could possibly be used to control the growth of proliferating cells and avoiding necrosis. The use of confluent monolayers of cells attached to the surface of alginate gel structures has the potential to be used in different applications in the manufacturing of producer systems or tissue constructs. Cells attached as spherical layers may be kept at a very high density while still allowing good availability for the exchange of nutrients, waste products as well as producer substance. However, for encapsulation applications involving the implantation of foreign cells additional coating procedures or macrocapsules protecting attached cells may be needed to make the use of the technology more practical. Also, cells entrapped within alginate beads covered with cells will, as a result of lack of nutrients, necessarily die.

Example 2

Introduction

Transplantation of biopolymer based tissue constructs holds a promising future in the treatment of a large number of diseases. Biocompatible biopolymers may be used to entrap cells within microbeads, thus protecting the cells against immune attack from the host and physical stress. Compared to other polymers, alginates, in particular, have good properties as immobilizing agents, a property which rests in the ability to form heat-stable gels that can develop and set at physiologically relevant temperatures. Cells entrapped in alginate beads excreting therapeutic molecules may be used as bioreactors in vivo in the treatment of a large variety of diseases, including cancer, diabetes, Parkinson's disease, chronic pain and liver failure. Therefore, alginates are now widely used as immobilizing materials for cells or tissue in the development of bioreactor systems for therapeutic use.

As an alternative to processing fresh organs shortly prior to medical use, growth of cells in vitro as a continuous source for bioreactor systems can also be used. Such cells can be genetically manipulated through well-known techniques to produce therapeutic products and are therefore attractive candidates in the development of new bioreactor systems. Different established cell lines immobilized in alginate beads have been studied and results are presented herein.

Methods

Cells from different established cell lines normally cultivated as monolayers in vitro were entrapped in alginate gel beads and their growth behavior was studied. The following cell lines were studied; Human HEK 293 Endo cells (embryonic kidney cells, transfected for endostatin production), human NHIK 3025 cells (cervix carcinoma in situ), canine MDCK cells (derived from an apparently normal kidney of an adult female cocker spaniel) and mouse C2C12 cells. The cells were first mixed with PRONOVA alginate solutions and entrapped in alginate beads of selected size using an electrostatic bead generator. Beads of different size ranging from 150 to about 600 µm were made by selecting different nozzles and operating the bead generator at an electrostatic potential of about 5 kV/cm. The alginate concentration was in most experiments 1.5 or 1.8% and the presence of $Na^+$ during gelling was avoided as much as possible by using mannitol (inhomogeneous beads). The gelling solution used was mostly 50 mM $CaCl_2$ or $SrCl_2$, but $BaCl_2$ was also tested. After gelling, the beads were transferred into monolayer cell culture flasks and normal cell growth medium was added. The growth medium was changed 2-3 times each week, and the beads were regularly transferred into new flasks in order to avoid extensive growth of cells released from the beads on the flask growth surface. The beads and cell growth were followed over time using light microscope or other techniques.

Results and Discussion

Figure 4:
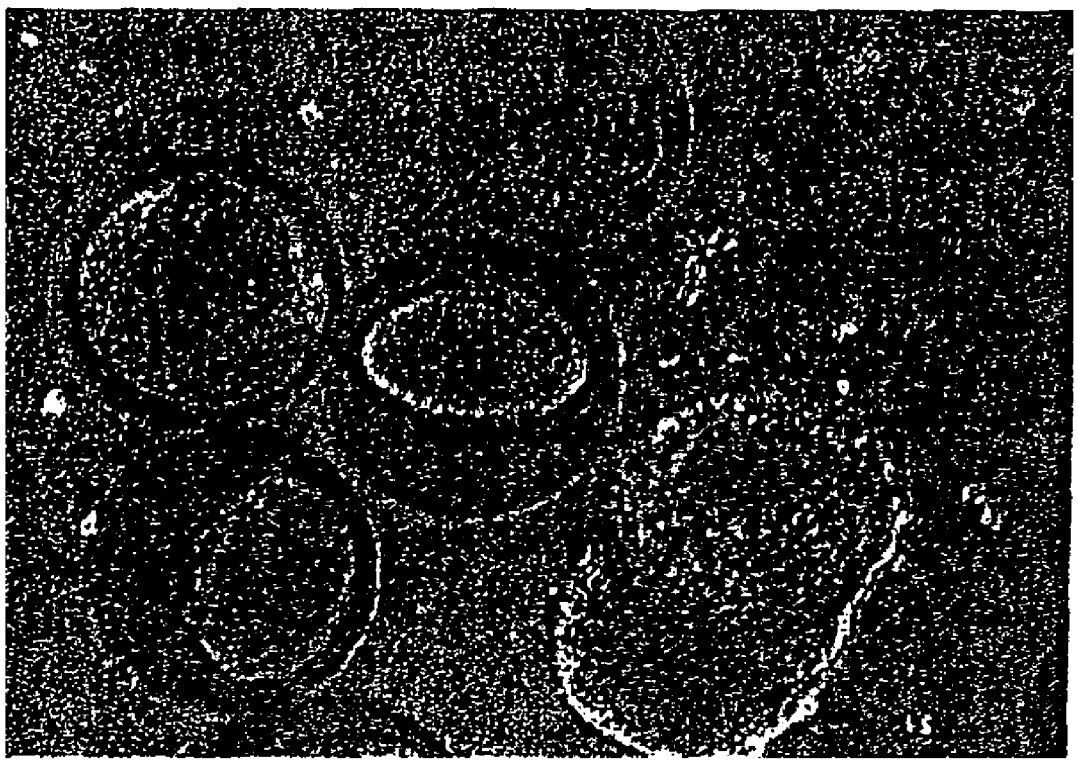
FIG. 4 is a light microscopy picture of HEK 293 Endo cells after 4 weeks in PRONOVA UP LVG alginate beads. Large colonies (spheroids) of growing cells can be seen in the bead center. The center of the spheroid will eventually become necrotized. The bead at bottom right shows cells growing at the bead surface and at the surface underneath.

Cells entrapped in alginate beads showed good viability during long term in vitro culture and there seemed to be no adverse effect on the cells by the alginate. This is consistent with already published data. Also in accordance with other published data, it was observed that cells entrapped in alginate gels continued to proliferate within the gel. The cells colonized large parts of the beads and even grew out of the beads. FIG. 4 shows HEK 293 Endo cells about one month after entrapment in alginate beads. As can be seen, large spheroids were formed within the beads and the cells also grew out of the beads. Some cells outside the beads stayed attached to the bead surface or grew outside the beads as cell aggregates. Proliferation of cells within alginate beads was dependent of the alginate gel (i.e. the type of alginate used as well as the gelling conditions). Generally low guluronic (G) content alginates, which produces a weaker gel network, more readily allowed cell proliferation. Cell proliferation was very limited during the first days for cells entrapped in a high G alginate. After some initial growth delay (typically 2-3 weeks) the cells started to grow more rapidly. This may be a result of weakening of the gel network during time due to the low content of gelling ions ($Ca^{2+}$) in the cellular growth medium. Gelling ions are therefore lost from the gel network, and thereby allowing a more readily cell proliferation.

The proliferation of cells within alginate gels can obviously be a problem for applications involving implantation of beads (or other structures) in humans or animals since such cell proliferation may cause bead degradation. Cells can also be expected to start to grow out of beads in vivo, and if so, cells of foreign origin will be exposed to the immune system of the host. This problem may be addressed as follows.

Figure 5:
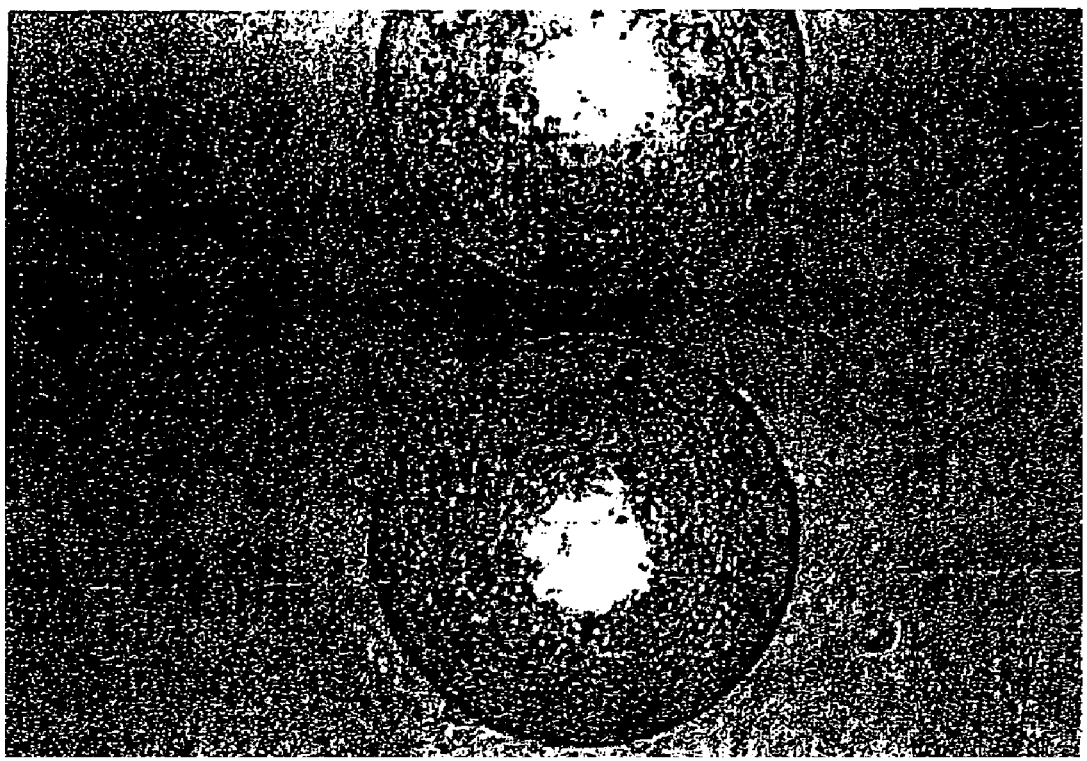
FIG. 5 shows a picture of calcium alginate (PRONOVA SLG) beads with MDCK cells. On one bead (bottom) the cells have completely covered the surface while the other growth on the surface has not yet started.

The growth behavior of different cell lines in calcium alginate beads has been studied and some clear differences in the growth pattern of different cells within and on the surface of alginate beads have been observed. In particular, MDCK cells were found to follow a surprisingly different growth pattern compared to the other cell lines studied. The MDCK cells were observed to grow on the surface of the beads as spherical monolayers covering the beads and without the formation of large cell aggregates in the solution. FIG. 5 shows pictures of two alginate beads, one covered with a complete spherical monolayer of cells and one bead with no growth at the surface. It was typical to see beads either completely covered or non-covered with cells during the growth period. This implied that colonizing of each beads was a rapid process as soon as it had been initiated (approximately one to two days). Some days after the initial outgrowth of cells, however, 100% of the beads were completely covered with cells. In contrast to the other cell lines studied, MDCK cells were growing on the surface of the beads as a regular spherical monolayer, and without large cell aggregates more or less attached on the surface. After the beads were covered with cells there was no further growth seen on the outside of the beads (confluence). However, it was observed that cells falling off from the beads were able to proliferate as normal monolayers attached to the cell cultivation surface. With fluorescence techniques and confocal imaging, cells in the spherical monolayer were shown to be viable for more than 5 months (the entire duration tested) while cells located within the beads were mostly dead. It was, however, possible that some proliferation occurred to replace single cells falling off the surface of the beads. MDCK cells attached to calcium alginate beads as a spherical monolayer were in a growth-inhibited state without any expansive proliferation within the beads or at the bead surface.

Figure 6:
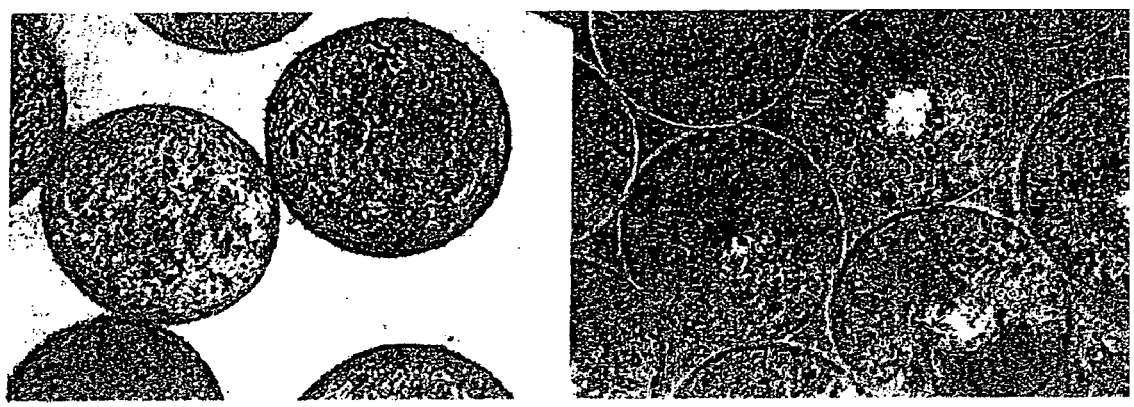
FIG. 6 shows a picture of MDCK cells in alginate beads after 4-6 months. The cells were entrapped in 1.8% PRONOVA UP LVG alginate in 50 mM $CaCl_2$ (left) and 50 mM $SrCl_2$ (right). For cells entrapped in calcium alginate 100% of the beads are completely covered with a spherical monolayer of cells while none of the other beads have cells attached on their surfaces. Some cell proliferation appears inside these beads although the beads are still intact.

Surprisingly it was discovered that cells only seemed to grow at the surface of calcium alginate gels and not on gels prepared with strontium as the gelling ion. Cells entrapped in strontium beads did not grow at all on the gel surface even after several months in culture while in parallel calcium beads, cells completely covered the beads in less than a month (FIG. 6). One explanation for this may be that the growth of cells at the calcium alginate surface is directly calcium dependent. For cells entrapped within alginate beads, the use of strontium seemed to be better than calcium as cell proliferation within the beads was much more limited and because cells did not grow on the surface of the beads. The viability of cells within strontium beads was, however, still good.

Figure 7:
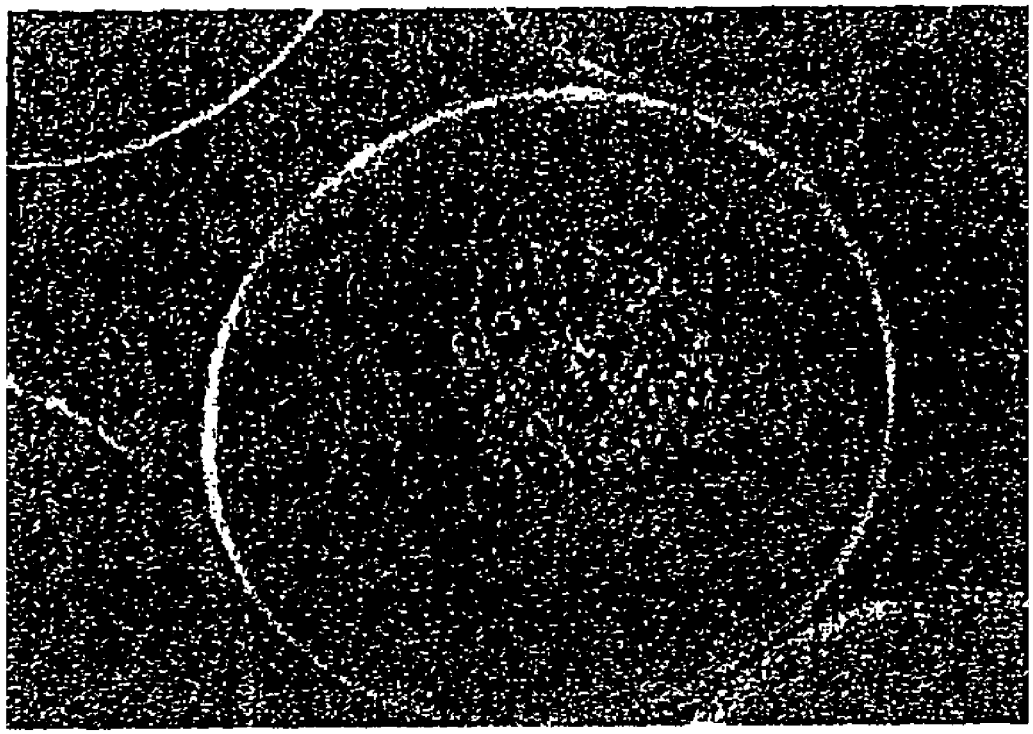
FIG. 7 shows a picture of a spherical monolayer of MDCK cells on calcium alginate beads entrapped in a larger alginate bead.

Alginate beads covered with spherical monolayer of cells can be subjected to a second entrapment in larger alginate beads or other gels structures (including encapsulation or containment using other biomaterials and/or devices) for further protection of the cells (FIG. 7). Beads may be coated with one or more layers of alginate or other biopolymer materials. This principle of controlling cell growth therefore may be used in different applications in the manufacturing of producer systems for in vivo or other applications. Cells attached as spherical monolayers may hold a very high cell number to bead volume concentration and the cells may also give good availability for the exchange of nutrients and production substance.

It is commonly observed that calcium alginate beads implanted into animals become completely covered with cells (lymphocytes, fibroblasts etc.) from the host. This ultimately leads to cell death of the entrapped cells because of lack of nutrients. Based upon in vitro observations of growing cells, this growth at the bead surface is ion-dependent and likely not related to adverse (immunologic) reactions of the host. Pure alginate beads gelled with strontium will not be covered with fibroblasts and therefore also be "more biocompatible." It is well known that cell attachment proteins are calcium dependent (cadherins and others). It is therefore possible that calcium associated with the gel network promotes the attachment of cells through association with calcium binding proteins.

Summary

Cells cultivated in vitro were observed to rapidly grow at the surface of an alginate gel. The cell growth on an alginate gel surface was gelling ion dependent. Cells only grew on calcium alginate gels and not on strontium gels. The growth pattern for cells varied between different cell lines and the initial growth must have been related to a rupture of the gel surface or protrusion of cells allowing anchorage dependent cell growth. Some cells, such as MDCK cells, covered the beads completely as a spherical monolayer. When the initial growth started, the beads were covered with cells within short time. The growth as spherical monolayers stopped further growth of cells within the beads (lack of nutrients). Cells covering beads completely as a spherical monolayer stopped proliferating at the surface due to inhibition because there was no more space to grow on. The growth seemed to follow the same principle as the growth on normal in vitro culture surfaces (i.e. confluency).

The selective growth of cells at the surface of calcium alginate gels and not on strontium suggests that the gelling ions plays a major role in the attachment of the cells to the bead surface, but also changes in the gel structure itself may be involved. Calcium from the gel network may affect anchorage dependent proteins (cadherins or others). Growing of cells on alginate surfaces can be used in tissue culturing applications. Alginate gels can be formed in different shapes, and devices with cells growing on them could be used for tissue construction and in grafts. The alginate gel could possibly also be removed after cell regrowth and this procedure could then be used to detach intact cell layers as a part of tissue engineering processes.

Compared to calcium gels, cell growth inside beads was inhibited in strontium gels that also demonstrated higher bead strength in general. Similarly, cell growth over Strontium beads was inhibited. Cell proliferation was inhibited in strontium and barium alginate beads.

In order to prevent unwanted cells from growing over beads (host fibroblasts and macrophages etc.), the beads covered with a spherical monolayer of cells may be further coated or subjected to double encapsulation for protection of the beads (i.e. physical protection or immunoprotection). This can be used as an optimized producer system with high cell concentrations thus having improved production capacity and cells may be kept viable for long time while the growth is controlled.

Alginate beads implanted in humans or animals may be subjected to immunological rejection. It has been observed that implanted alginate beads become covered with growing cells (lymphocytes, fibroblasts etc.). The present observations indicate that the attachment and growth of host cells on alginate beads in vivo is not necessarily always caused by an immunologic reaction as the calcium containing gel surface may be an anchorage substrate for cell attachment and proliferation. Cell overgrowth of implanted beads is thus inhibited by incorporating Strontium within the alginate matrix containing cells. An additional manner would be to incorporate calcium beads having cells grown on the outer surface as a monolayer immobilized within a strontium gelled matrix.

The invention claimed is:

1. A method of inhibiting cell growth on a surface of an implantable composition comprising cells in an animal for 180 or more days comprising the step of maintaining the implantable composition in the animal's body for 180 or more days wherein said surface of the implantable composition comprises an alginate gel comprising Strontium.

2. The method of claim 1 wherein the implantable composition further comprises physiologically active compounds, proteins or peptides encapsulated with the alginate matrix.

3. The method of claim 1 wherein the cells in said implantable composition comprise an expression vector that encodes a protein that is expressed when the cells are maintained.

4. The method of claim 1 wherein the alginate matrix is spheroidal with a cross section of between about 20 and about 600 µm.

* * * * *